United States Patent [19]
Cahill et al.

[11] Patent Number: 5,475,172
[45] Date of Patent: Dec. 12, 1995

[54] PROCESS FOR FULLERENE FUNCTIONALIZATION

[75] Inventors: Paul A. Cahill, Albuquerque, N.M.; Craig C. Henderson, Dublin, Calif.

[73] Assignee: Sandia Corporation, Albuquerque, N.M.

[21] Appl. No.: 160,345

[22] Filed: Dec. 1, 1993

[51] Int. Cl.$^6$ ............................ C07C 1/00; C07C 13/62; C01B 31/00
[52] U.S. Cl. ............................ 585/27; 585/22; 585/266; 585/271; 585/469; 585/943; 423/445 B
[58] Field of Search ................. 423/445 B, DIG. 39, 423/DIG. 40; 585/943, 22, 26, 27, 266, 271, 469

[56] References Cited

PUBLICATIONS

Chandrasekharan, S., "Organic Chemistry with Buckminsterfullerene ($C_{60}$)", Indian Journal of Chemistry, vol. 31 A and B, May 1992, pp. F36–F41.
Taylor et al., Nature., vol. 363 pp. 685–693 Jun. 24, 1993.
Welch et al., Journal of Chromatography vol. 609, pp. 89–101 Sep. 18, 1992.
Chiang et al., Journ. Am. Chem. Soc., 114(26) pp. 10154–10157 Dec. 16, 1992.
Chiang et al., Journ. Chem. Soc., Chem. Commun., No. 24, Dec. 15, 1992.
Ballenweg et al., Tetrahedron Letters, 34(23) pp. 3737–3740, Jun. 4, 1993.
Rao et al. [Indian Journal of Chemistry, vol. 31, pp. F27–F31, May 1993.
Schneider et al., J. Chem. Soc. Chem. Comm., pp. 463–464, Feb. 21, 1994.
Kroto, H. W., et al, Nature, "$C_{60}$: Buckminsterfullerene," vol. 318, pp. 162–163, (Nov. 1985).
Kratschmer, W., et al, Nature, "Solid $C_{60}$: A New Form of Carbon," vol. 347, pp. 354–358, (Sep. 1990).
Haufler, R. E., et al., J. Phys. Chem., "Efficient Production of $C_{60}$ (Buckminsterfullerene), $C_{60}H_{36}$, and the Solvated Buckide Ion," vol. 94, pp. 8634–8636, (1990).
Taylor, R., J. Chem. Soc. Perkin Trans. 2, "$C_{60}$, $C_{70}$, $C_{76}$, $C_{78}$, $C_{84}$: Numbering, $\pi$–Bond Order Calculations and Addition Pattern Considerations," pp. 813–824, (1993).
Friedman, et al., J. Am. Chem. Soc., "Inhibition of the HIV–1 Protease by Fullerene Derivatives: Model Building Studies and Experimental Verification," vol. 115, pp. 6506–6509, (1993).
Sijbesma, R., et al. J. Am. Chem. Soc., "Synthesis of a Fullerene Derivative for the Inhibition of HIV Enzymes," vol. 115, pp. 6510–6512, (1993).
Schinazi, R. F. et al, Antimicrobial Agents and Chemotherapy, "Synthesis and Virucidal Activity of a Water–Soluble, Configurationally Stable, Derivatized $C_{60}$ Fullerene," vol. 37, No. 8, pp. 1707–1710, (Aug., 1993).
Welch, C. J. et al, Journal of Chromatography, "Progress In The Design of Selectors For Buckminsterfullene," vol. 609, pp. 89–101, (1992).
Baum, R., Chemical and Engineering News, "Fullerene Bioactivity $C_{60}$ Derivative Inhibits AIDS Viruses," pp. 3–4, (aug. 1993).

Primary Examiner—Michael Lewis
Assistant Examiner—Peter T. DiMauro
Attorney, Agent, or Firm—George H. Libman; Timothy D. Stanley

[57] ABSTRACT

Di-addended and tetra-addended Buckminster fullerenes are synthesized through the use of novel organoborane intermediates. The $C_{60}$, $C_{70}$, or higher fullerene is reacted with a borane such as $BH_3$ in a solvent such as toluene to form an organoborane intermediate. Reaction of the organoborane such as hydrolysis with water or alcohol results in the product di-addended and tetra-addended fullerene in up to 30% yields. Dihydrofullerenes and tetrahydrofullerenes are produced by the process of the invention.

22 Claims, 2 Drawing Sheets

PROCESS FOR FULLERENE FUNCTIONALIZATION

The United States Government has rights in this invention pursuant to Contract No. DE-AC04-76DP00789 between the Department of Energy and American Telephone and Telegraph Company.

BACKGROUND OF THE INVENTION

The present invention relates to a novel process for producing di-addended and tetra-addended Buckminster fullerenes, Still more particularly, this invention relates to a novel process for producing di-addended and tetra-addended Buckminster fullerenes through the use of novel organoborane intermediates.

DESCRIPTION OF THE PRIOR ART

Buckminster fullerene molecules (fullerenes), also known as "buckyballs" are hollow molecules of 60, 70, or more carbon atoms whose configuration resembles geodesic domes (See H. W. Kroto et al, *Nature*, 318, p. 162 (1985) and W. Kratschmer, *Nature*, 347, p. 352 (1990).

The synthesis of macroscopic amounts of $C_{60}$ has generated much interest in the physical and chemical properties of this spherical molecule. Fully characterized synthetic derivatives of $C_{60}$ have largely been limited to the epoxide, $C_{60}O$, $C_{60}CR_2$ fulleroids and related compounds, osmate esters, polybrominated derivatives, and organometallic compounds, including several iridium and platinum complexes.

Previous attempts to prepare the di-addended fullerenes such as the dihydrofullerene of $C_{60}$ failed due to the reactivity of the $C_{60}$ molecule. Previous efforts resulted in additions in a large number of sites on the $C_{60}$ molecule resulting in "hairy balls" which do not have the desired chemical properties.

In the present invention the simplest $C_{60}$ hydrocarbon derivatives, $C_{60}H_2$, $C_{60}H_4$, and $C_{70}$ hydrocarbon derivation, $C_{70}H_2$ are prepared. Preparation of the dihydro-$C_{60}$ or $C_{70}$ illustrates the potential of the novel fullerene based organoborane compounds of the present invention as intermediates in the preparation of a large class of compounds potentially useful as pharmaceuticals, electronic or photonic materials, and high strength materials.

SUMMARY OF THE INVENTION

The present invention relates to the formation of a class of di-addended and tetra-addended fullerenes by the employment of novel organoborane fullerene intermediate technology.

An object of the invention is to provide a process for preparing di-addended and tetra-addended fullerenes.

A further object of the present invention is to provide a process for preparing di-addended and tetra-addended fullerenes employing organoborane fullerene intermediates.

A still further object of the present invention is to provide a process for preparing tetra-addended fullerenes employing organoborane fullerene intermediates followed by hydrolysis to the desired tetra-addended fullerenes.

A still further object of the present invention is to provide a novel class of compounds, dihydro- and tetrahydro-fullerenes.

A still further object of the present invention is to provide a novel class of compounds, organoborane fullerene intermediates useful for the preparation of addended fullerenes.

Additional objects, advantages, and novel features of the invention will become apparent to those skilled in the art upon examination of the following description or may be learned by practice of the invention. The objects and advantages of the invention may be realized and attained by means of the processes particularly pointed out in the appended claims.

To achieve the foregoing and other objects, and in accordance with the purpose of the present invention, as embodied and broadly described herein, the present invention describes a method for preparing a di-addended or tetra-addended fullerene comprising the steps of: (A) reacting a fullerene with a borane to form an organoborane intermediate compound; (B) hydrolyzing said organoborane intermediate compound to form an addended fullerene product mixture; and (C) separating the addended fullerene product from said product mixture.

BRIEF DESCRIPTION OF THE DRAWINGS

The accompanying drawings, which are incorporated in and forms part of the specification further illustrate the present invention and, together with the description, serve to explain the principles of the invention.

DETAILED DESCRIPTION OF THE INVENTION

The preparation of the dihydro and tetrahydro derivatives of Buckminster Fullerene, $C_{60}H_2$, $C_{60}H_4$, or $C_{70}H_2$ illustrate the desirability of the novel fullerene-based organoborane intermediates. They are desirable because of their potential to act as intermediates in forming a new class of compounds, di-addended and tetra-addended fullerenes. New high-strength materials, new electronic materials, and new pharmaceuticals are among the potential products to be derived from di-addended and tetra-addended fullerenes.

Figure 1A:
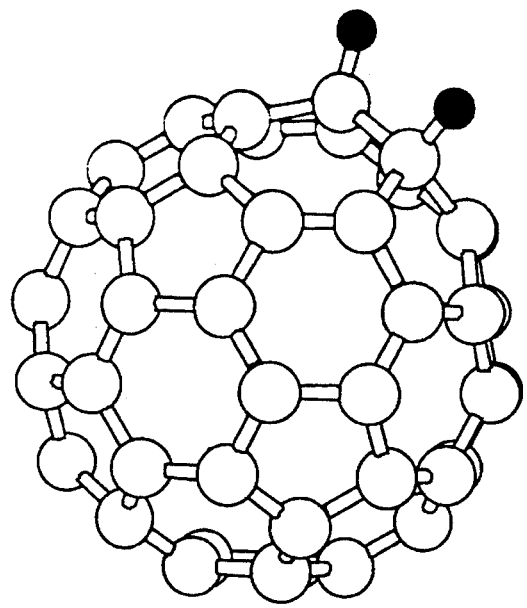
FIG. 1A is a graphic illustration of the 1,2 isomer of the dihydro-fullerene molecule $C_{60}H_2$ (light dots represent carbon atoms and dark dots represent added hydrogen atoms).
Figure 1C:
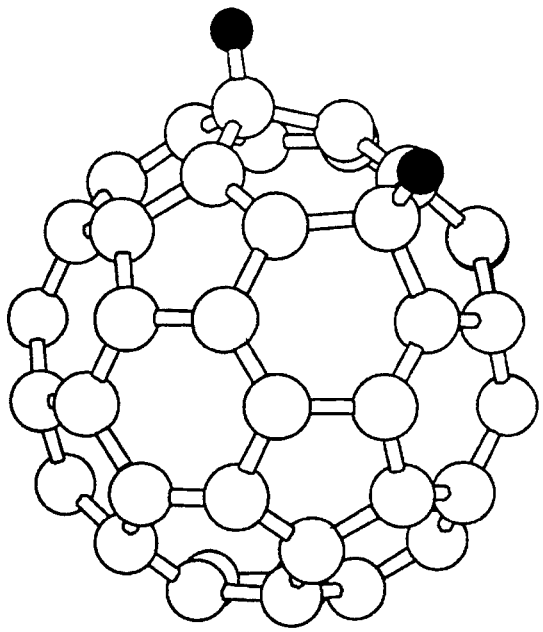
FIG. 1C is a graphic illustration of the 1,11 isomer of the dihydro-fullerene molecule $C_{60}H_2$.
Figure 1B:
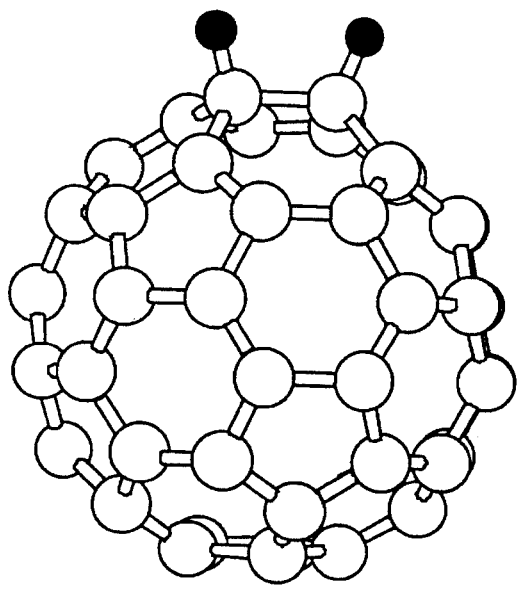
FIG. 1B is a graphic illustration of the 1,6 isomer of the dihydro-fullerene molecule $C_{60}H_2$.
Figure 2A:
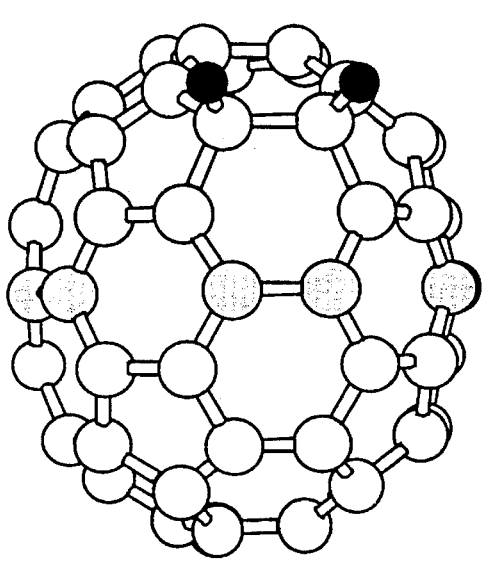
FIG. 2A is a graphic illustration of the 7,8 isomer of the dihydro-fullerene molecule $C_{70}H_2$.
Figure 2B:
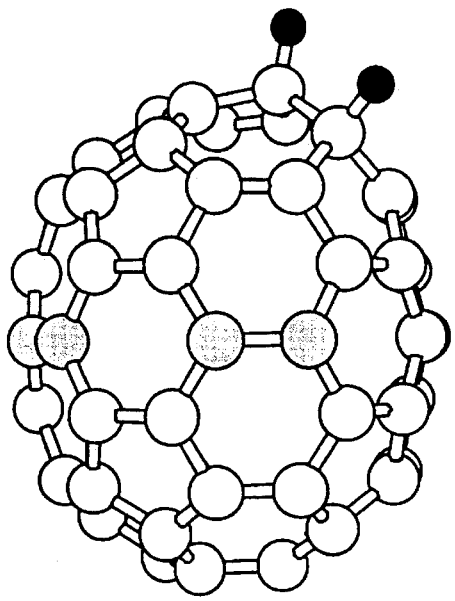
FIG. 2B s a graphic illustration of the 1,9 isomer of the dihydro-fullerene molecule $C_{70}H_2$.
Figure 2C:
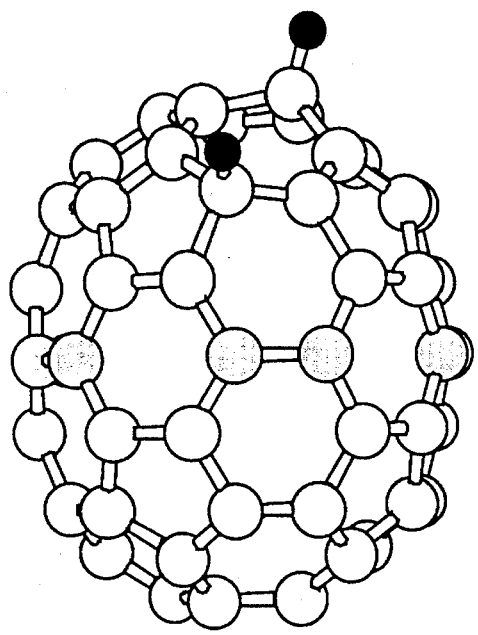
FIG. 2C is a graphic illustration of the 1,7 isomer of the dihydro-fullerene molecule $C_{70}H_2$.
Figure 2D:
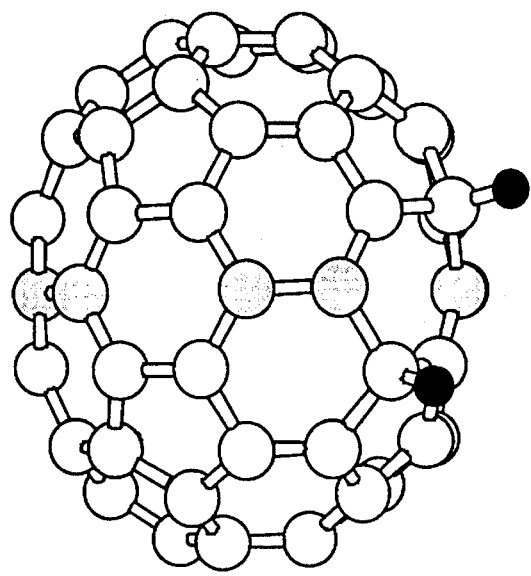
FIG. 2D is a graphic illustration of the 21,42 isomer of the dihydro-fullerene molecule $C_{70}H_2$.

The synthesis of $C_{60}H_2$ appeared to be a reachable goal based upon the inventors computational studies directed toward identifying which, if any, of the 23 isomers of $C_{60}H_2$ would be preferentially populated at equilibrium at room temperature. These computational studies were made to gain insight into which, if any, of the 23 isomers of $C_{60}H_2$ would be preferentially populated at equilibrium at room temperature. A nomenclature system was employed according to R. Taylor, *J. Chem. Soc. Perkin Trans.* 2 813 (1993). This system is a clockwise spiral numbering in which the carbon atoms in a fullerene are numbered consecutively from the hexagonal cap of its longest axis of symmetry through to the opposite hexagonal cap. Addition of functional groups, such as $H_2$ addition to a 6,6 or 6,5 ring fusion is then identified by the carbon label, for example, 1,2-$C_{60}H_2$ or 1,6-$C_{60}H_2$, respectively. Semiempirical calculations suggested that the 1,2 and 1,11 isomers of $C_{60}H_2$ have the lowest heats of formation, with the 1,11 isomer (1,4 addition across a 6-ring) having a heat of formation 3.8 kcal/mol higher in energy. See FIG. 1A, 1B, and 1C representing 1,2, 1,6, and 1,11 isomers of $C_{60}H_2$, respectively. (The dark dots represent addended hydrogen atoms.) Similar calculations on the 143 isomers of $C_{70}H_2$ indicate that four isomers, 7,8, 1,9, 1,7, and 21,42 have the lowest heats of formation. See FIG. 2A, 2B, 2C, and 2D representing 7,8, 1,9, 1,7, and 21,42 isomers of $C_{70}H_2$, respectively.

Methods are known to produce $C_{60}$ polyhydride mixtures by reduction. (See R. E. Haufler et al, *J. Phys. Chem.*, 94, 8634 (1990). Known methods, however, had not produced the desired di-substituted dihydride.

It has been discovered that di-addended fullerenes such as dihydro-fullerenes, $C_{60}H_2$, can be produced in high yields by the reaction of $C_{60}$ with borane to form the intermediate $C_{60}(H)(BH_2)$ according to the following reaction:

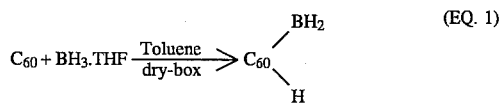

(EQ. 1)

The inventive intermediate product may be subjected to reaction such as hydrolysis to form the di-addended fullerene product as illustrated by the formation of $C_{60}H_2$ by the following reaction:

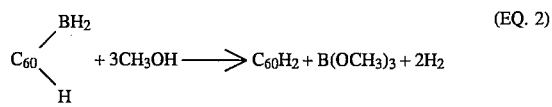

(EQ. 2)

In the more general case the inventive process may be described as the reaction of $HBR_2$, $BCl_2H$, or $RBClH$, where R=hydrogen, carbon, such as alkyl or phenyl or combined alkyl and phenyl, or a heteroatom, with $C_{60}$ or $C_{70}$ in a suitable solvent for a specified time, at a specified temperature or range of temperatures under dry and oxygen-free conditions. The borane employed as a reactant can be used in a form complexed with ethers, such as tetrahydrofuran, or thioethers, such as dimethylsulfide, or other compounds; or in an uncomplexed form. The desired solvent is capable of dissolving both of the reagents while not reacting with either of them. Example of solvents useful in the practice of the present invention are ethers such as tetrahydrofuran (THF), aromatics such as toluene, and sulfides such as dimethyl sulfide.

The desirable temperature range for reaction of $C_{60}$ is from −20° C. to 50° C., with a preferred temperature of about 0° C. Good yields, approximately 30%, are obtained from adding 2 equivalents of 1 Molar borane:tetrahydrofuran to a saturated solution of $C_{60}$ in dry toluene under argon at 0° C., stirring for 45 minutes, and warming to room temperature. The intermediate borane formed in this process can be hydrolyzed with water to form a mixture of $C_{60}H_2$ and $C_{60}H_4$ which can be subjected to separation to obtain the desired dihydro derivative.

The following examples further illustrate the present invention.

EXAMPLE 1

The reaction of $C_{60}$ with $BH_3$:tetrahydrofuran in toluene was performed according to the above procedure and followed by hydrolysis, yielding a $C_{60}H_2$ reaction mixture. This product was separated by high-performance liquid chromatography, employing a Buckyclutcher I column, available from SES Research, Inc., Houston, Tex., (See *J. Chromatography*, 609, 89–101, (1992), and the product characterized as the addition product of $H_2$ to a 6,6-ring fusion (1,2 isomer). The $^1H$ nuclear magnetic resonance (NMR) spectrum of the product remained a sharp singlet between −80° and +100° C., which suggests a static structure on the NMR time scale. The sharp singlet resonance (0.5-Hz full width at half maximum) at δ5.93 ppm in the $^1H$ NMR spectrum was observed immediately upon hydrolysis of the reaction mixture. This chemical shift is downfield of chemical shifts for both difluorenyl (δ4.81 ppm) and triphenylmethane (δ5.57 ppm). The low-field chemical shift is thus consistent with known compounds if the electron-withdrawing effect of the fullerene is taken into account. Hydrolysis of the proposed borane addition product with acetic acid-$d_1$ or $D_2O$ yielded $C_{60}HD$, and its $^3J_{HD}$ coupling constant is consistent with vicinal addition. The observation of a single $C_{60}H_2$ isomer is in complete agreement with earlier calculations that indicated that at most 2 of the 23 possible isomers of $C_{60}$ would be observable at equilibrium m room temperature.

The desirable temperature range for reaction of $C_{70}$ is from 0° C. to 70° C. with a preferred temperature of about 22° C. or room temperature. Good yields, approximately 20%, are obtained by adding 2 equivalents of 1 Molar borane:tetrahydrofuran to a saturated solution of $C_{70}$ in dry toluene under argon at room temperature (about 22° C.) and stirring for 45 minutes. The intermediate borane formed in this process can by hydrolyzed with water to form $C_{70}$ as a mixture of two isomers.

EXAMPLE 2

The reaction of 2 equivalents of $BH_3$(1M in THF) with $C_{70}$ in toluene (0.5 mg/mL) at 22°–25° C. for 1 hour with subsequent hydrolysis with water resulted in a product mixture containing a 1:2 mixture of 7,8 and 1,9-$C_{70}H_2$ in 20% overall yield. The order of elution on a Buckyclutcher I stationary phase with a 60:40 toluene:hexane isocratic mobile phase is $C_{60}$ (impurity), $C_{70}$, 7,8-$C_{70}H_2$ and 1,9-$C_{70}H_2$. Minor, uncharacterized products were also observed at longer elution times. Isolation, concentration and-separation of the $C_{70}H_2$ products has led to pure samples of each isomer the High resolution FAB mass spectrum of these compounds confirmed the above assignment of the molecular formula.

The $^1H$ NMR spectrum of the first eluting isomer in toluene-$d_8$ consists of an AB quartet centered at δ3.91 ppm. The spectrum of the corresponding $C_{70}HD$ isomer formed by hydrolysis of the intermediate organoborane with $D_2O$ shows $^3J_{HD}$ of 2.3±0.2 Hz and a small upfield isotope shift $^3\Delta H(D)$ of 8.4 ppb, consistent with vicinal equivalent hydrogens. Of the possible products resulting from addition to 6:6-ring fusions, only the 7,8-,21,22-, and 23,34-$C_{70}H_2$ isomers would have spectra consistent with these data. The significantly lower heat of formation calculated at the MNDO level for the 7,8 isomer led to the final structure assignment.

The $^1H$ NMR spectrum of the second eluting isomer in toluene-$d_8$ consists of an AB quartet centered at δ4.00 ppm. Simulation of the spectrum leads to a $(v_A-v_B)$ of 204 Hz and a $^3J_{HH}$ of 16.1 Hz. The spectrum of the corresponding $C_{70}HD$ isomer also shows a $^3H_{HD}$ of 2.2±0.2 Hz and a small upfield isotope shift $^3\Delta H(D)$ of 7.8 ppb, all consistent with vicinal, nonequivalent hydrogens. Only the 1,9 structure can be assigned to this product on the basis of calculated heats of formation.

EXAMPLE 3

To a solution of 10 mg (14 μmol) of $C_{60}H_2$ (synthesized as in Example 1, above) in 15 mL of toluene, was added 14 μL of 1.0M $BH_3$ in THF at 0° C. under argon at once. The mixture was stirred a 0° C. for 45 minutes, warmed to room temperature for 45 minutes, and quenched by addition of 1.0 mL of water. The organic layer was separated, dried over $MgSO_4$, and product isolated by preparative chromatography on a 10 mm×25.0 cm Buckyclutcher I column with a 50:50 toluene:hexane mobile phase. The yield of this reaction is about 10%, less than the 20–30% yields of $C_{60}H_2$ that are obtained from $C_{60}$ under similar conditions ($C_{60}H_4$ isomers were first obtained as side products in <1% yields in this reaction). The UV/Vis spectrum of this isomer in 50:50 toluene:hexane tails from 290 nm with a shoulder at 342 nm and a weak, but distinct absorption at 442 nm, both of which may be diagnostic for this substitution pattern. MS, positive ion, FAB: observed, 724.0309; calculated, 724.0313.

It is anticipated that the novel fullerene organoborane technology of the present invention can be applied to the production of new materials and the preparation of new pharmaceuticals. An example of the use of functionalized fullerenes as pharmaceuticals is di(phenethylaminesuccinate) fulleroid, made by adding a substituted diphenyldiazomethane to $C_{60}$. This substance has been shown to have a virucidal effect on HIV-1 and HIV-2, the viruses to which Acquired Immune-Deficiency Syndrome (AIDS) disease is attributed. The fulleroid appears to inhibit reverse transcriptase and HIV-1 protease, and also appears to kill the viruses, themselves. (See R. Baum, *Chemical and Engineering News*, August (1993), *J. Am. Chem. Soc.*, 115, 6506 and 6510 (1993), and *Antimicrobial Agents and Chemotherapy*, 37, 1707 (1993). The organoborane intermediate approach of the present invention is useful in the preparation of functionalized fullerenes such as the fulleroid discussed above.

The employment of functionalized fullerenes in polymers is illustrated by Taylor et al., *Nature*, 363, 685 (1993) at p. 691. The organoborane intermediate approach of the present invention is useful in the preparation of monomers useful in the preparation of the polymers described therein. One application for such polymers is in photoconductive applications for reproduction equipment including photocopiers and laser printers. Addition to a fullerene is known to change both the optical (absorption of light) and electronic properties (redox potentials—i.e., the relative ease of addition or removal of an electron(s)) of the fullerene. Therefore, functionalized fullerenes my be useful in enhancing the photoconductive properties of polymers (including $C_{60}H_2$) containing such molecules.

The particular processes and examples discussed above are cited merely to illustrate a particular embodiment of this invention. It is contemplated that the practice of the invention may involve additional process steps as long as the principle, the functionalization of fullerenes through organoborane intermediates is followed. The invention contemplates other derivative process steps. It is intended that the scope of the invention be defined by the claims appended hereto.

We claim:

1. A method for preparing a di-addended or tetra-addended fullerene comprising the steps of:

A) reacting a non-addended or di-addended fullerene reactant with a borane under conditions effective to form an organoborane intermediate compound capable of being hyrolyzed to form a di- or tetra-addended fullerene;

B) hydrolyzing said organoborane intermediate compound to form said di- or tetra-addended fullerene product mixture; and C) separating and recovering said di- or tetra-addended fullerene product from said product mixture.

2. The method of claim 1 wherein said fullerene reactant is selected from the group consisting of $C_{60}$, $C_{60}H_2$, and $C_{70}$.

3. The method of claim 2 wherein said step A is carried out in a dry liquid solvent medium.

4. The method of claim 3 wherein said borane is selected from the group consisting of $HBR_2$, where R is hydrogen, alkyl, or phenyl.

5. The method of claim 4 wherein said borane is present in complexed form.

6. The method of claim 5 wherein said borane is complexed with a compound selected from the group consisting of ethers and thioethers.

7. The method of claim 6 wherein said ether is tetrahydrofuran.

8. The method of claim 6 wherein said thioether is dimethylsulfide.

9. The method of claim 3 wherein said liquid solvent medium is toluene.

10. The method of claim 9 wherein said borane is borane:tetrahydrofuran, said non-addended or di-addended fullerene reactant is in a saturated solution, and said borane:tetrahydrofuran is added to said non-addended or di-addended fullerene solution in about a 2 to 1 molar ratio of borane to fullerene reactant.

11. The method of claim 10 wherein said non-addended fullerene reactant is $C_{60}$ and said reaction is carried out at a temperature in the range of about −20° C. to about +50° C.

12. The method of claim 11 wherein said reaction is carried out at a temperature of about 0° C.

13. The method of claim 10 wherein said non-addended fullerene reactant is $C_{70}$ and said reaction is carried out at a temperature in the range of about 0° C. to about +70° C.

14. The method of claim 13 wherein said reaction is carried out at a temperature of about +22° C. or room temperature.

15. The method of claim 10 wherein said di-addended fullerene reactant is $C_{60}H_2$ and said reaction is carried out at a temperature in the range of about −20° C. to about +50° C.

16. The method of claim 10 wherein said reaction is carried out at a temperature of about 0° C.

17. The method of claim 1 wherein said hydrolysis step is carried out with a compound selected from the group consisting of $H_2O$ and methyl alcohol at a temperature of about 22° C. or room temperature.

18. The di- or tetra-addended fullerene product of the method of claim 1.

19. The di- or tetra-addended fullerene product of the method of claim 11.

20. The di- or tetra-addended fullerene product of the method of claim 13.

21. The di- or tetra-addended fullerene product of the method of claim 15.

22. The compound $C_XH_Y$, where X=60 or 70 and Y=2 or 4.

* * * * *